(12) United States Patent
Poortinga et al.

(10) Patent No.: US 8,637,104 B2
(45) Date of Patent: Jan. 28, 2014

(54) MICROENCAPSULATE AND PROCESS FOR THE MANUFACTURE THEREOF

(75) Inventors: Albert Thijs Poortinga, Apeldoorn (NL); Daniela Oana Trambitas, Voorburg (NL); Gerard Willem Hofland, Hoogmade (NL)

(73) Assignees: Feyecon B.V., Haarlem (NL); Friesland Brands B.V., Meppel (NL)

( * ) Notice: Subject to any disclaimer, the term of this patent is extended or adjusted under 35 U.S.C. 154(b) by 104 days.

(21) Appl. No.: 13/056,969

(22) PCT Filed: Jul. 31, 2009

(86) PCT No.: PCT/NL2009/050475
§ 371 (c)(1),
(2), (4) Date: Mar. 1, 2011

(87) PCT Pub. No.: WO2010/014011
PCT Pub. Date: Feb. 4, 2010

(65) Prior Publication Data
US 2011/0171349 A1   Jul. 14, 2011

(30) Foreign Application Priority Data

Jul. 31, 2008   (EP) .................................... 08161556

(51) Int. Cl.
*A23L 1/00*   (2006.01)
*A23L 1/216*   (2006.01)

(52) U.S. Cl.
USPC ............................................. 426/89; 426/96

(58) Field of Classification Search
None
See application file for complete search history.

(56) References Cited

U.S. PATENT DOCUMENTS 3,821,422 A   6/1974 Morse et al.
(Continued)

FOREIGN PATENT DOCUMENTS

| GB | 2 226 804 A | 12/1989 |
|---|---|---|
| WO | WO 98/13136 | 4/1998 |
| WO | WO 2008/056344 A2 | 5/2008 |

OTHER PUBLICATIONS

International Search Report for related International Patent Application No. PCT/NL2009/050475, completed Oct. 6, 2009.

(Continued)

*Primary Examiner* — Humera Sheikh
*Assistant Examiner* — Subbalakshmi Prakash
(74) *Attorney, Agent, or Firm* — Gilberto M. Villacorta; Sunit Talapatra; Foley & Lardner LLP

(57) ABSTRACT

The present invention relates to a microencapsulate comprising microcapsules having a diameter of 0.1 μm to 25 μm, said microcapsules comprising: —a core particle having a diameter of 90 nm to 23 μm and containing at least 3% of the active component by weight of said core particle; and —a coating that fully envelops the core particle and containing at least 20 wt. % of a hydrophobic polymer selected from cellulosic ethers, cellulosic esters, zein, shellac, gluten, polylactide, hydrophobic starch derivatives, polyvinyl acetate polymers, polymers or copolymers derived from an acrylic acid ester and/or a methacrylic acid ester and combinations thereof; wherein the core particle contains a release trigger component and/or the coating contains a release trigger component, said release trigger component being selected from: —a water-swellable polymer having a water-uptake capacity at 37° C. and pH 7.0 of less than 20 wt. % and a water-uptake capacity at 37° C. and pH 2.0 of at least 50 wt. %; and—an edible salt having a water solubility at 37° C. and a pH of 7.0 of less than 1 mg/ml and a water solubility at 37° C. and a pH of 2.0 of at least 5 mg/ml; The microencapsulate of the present invention does not release the encapsulated active component when incorporated in water-containing foodstuffs, beverages, nutritional compositions or pharmaceutical compositions. Following ingestion, however, the active component is released rapidly.

5 Claims, 1 Drawing Sheet

(56) References Cited

Figure 1:
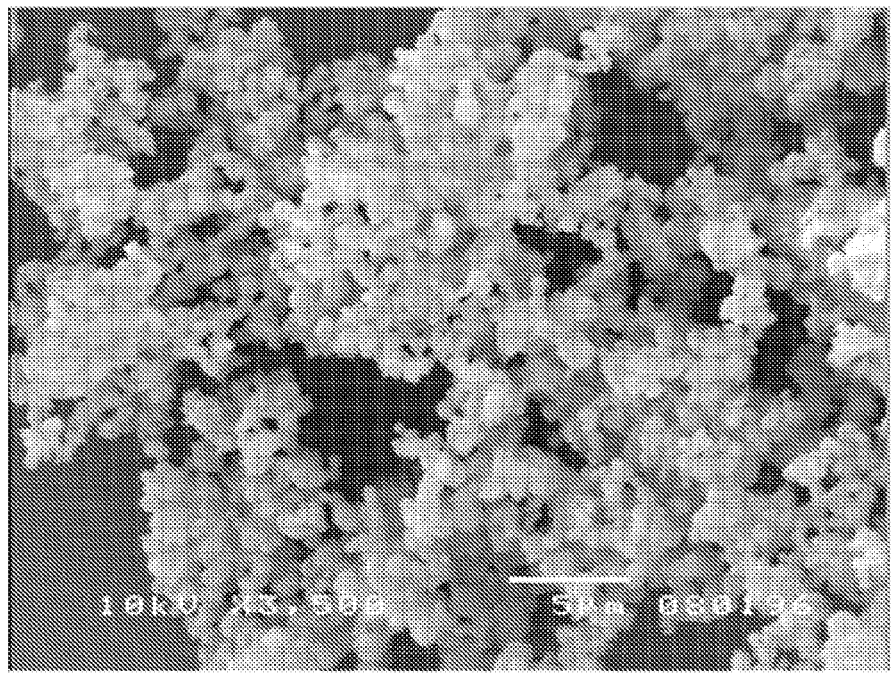

U.S. PATENT DOCUMENTS 4,462,982 A * 7/1984 Samejima et al. ............ 424/495
5,531,735 A * 7/1996 Thompson ................. 604/891.1
6,183,783 B1 * 2/2001 Benoit et al. .................. 424/497
6,531,152 B1   3/2003 Lerner et al.

OTHER PUBLICATIONS

International Preliminary Report on Patentability for related International Patent Application No. PCT/NL2009/050475, completed Oct. 29, 2010.

* cited by examiner

US 8,637,104 B2

MICROENCAPSULATE AND PROCESS FOR THE MANUFACTURE THEREOF

TECHNICAL FIELD OF THE INVENTION

The present invention relates to a microencapsulate and to a process for the manufacture thereof. More particularly, the present invention relates to a microencapsulate comprising microcapsules that contain a core particle holding an active component and a coating made of a hydrophobic polymer that fully envelops said core particles. The hydrophobic nature of the coating ensures that the coating will not, or will only slowly dissolve in water. Thus, the active component can be protected efficiently against moisture. Furthermore, the release of the active component from the microcapsule in aqueous environment can be controlled effectively.

BACKGROUND OF THE INVENTION

Micro-encapsulation is a process in which tiny particles or droplets are surrounded by a coating to give small capsules that have many useful properties. In a relatively simplistic form, a microcapsule is a small particle or droplet with a uniform shell around it. The small particle or droplet inside the microcapsule is referred to as the core, internal phase, or fill, whereas the shell is sometimes called a coating, a wall or membrane.

The reasons for microencapsulation are countless. Examples of possible uses of microencapsulation include:
  prevention of adverse interactions between the core material of the microcapsules and the environment of these microcapsules (atmosphere, product matrix, stomach etc.)
  improvement of the handling properties of the core material (e.g. by improving dispersibility or reducing stickiness)
  manipulation of the rate at which the core material can participate in dynamic processes (e.g. controlled release of drugs or pesticides)
  masking of the taste or odour of the core material.

A huge variety of materials has been used as coating agents in the preparation of microcapsules. These materials include hydrophilic coating agents such as maltodextrin, alginate, gelatine, whey protein, hydroxy propyl methylcellulose, sucrose etc. Hydrophilic coating agents are particularly useful in case the microcapsules need to quickly release the core material when brought into contact with water. For some applications, however, it is important that the core material is not released when the microcapsules come into contact with water or that is only released when additionally a certain release trigger is provided (e.g. pH release). For the latter applications hydrophobic coating agents have been used as coatings made of these hydrophobic agents tend to be stable in the presence of water. Examples of hydrophobic coating agents that have been used in the manufacture of microcapsules include cellulosic ethers, zein, polylactide, OSA etc.

U.S. Pat. No. 3,821,422 describes a method of microencapsulating thiamine in a continuous ethylcellulose coating. The method described in the examples of the US patent involves dissolving ethylcellulose, polyethylene and thiamine in cyclohexane at 80° C., followed by cooling. As the temperature drops, solvated ethylcellulose develops as a separate phase due to the presence of polyethylene (polymer/polymer incompatibility). The solvated ethylcellulose distributed in the cyclohexane as droplets is said to tend to wet individual granules of thiamine and to envelop them. As the temperature drops further, the ethylcellulose looses solvent and develops in solid encapsulating walls. The microcapsules are said to protect the thiamine in the preparation of dough or batter, at elevated processing temperature and in the final product. Moreover, it is observed that the thiamine is released in the digestive juices of the gastrointestinal tract.

U.S. Pat. No. 4,462,982 describes ethylcellulose microcapsules wherein a polymer material which shows at least 1.2 times increase in weight by immersing it in water at 37° C. is incorporated into the ethylcellulose coating walls and/or the core material thereof. The examples of the US patent describe a process in which the microcapsules are prepared by dissolving ethylcellulose in cyclohexane, dispersing a core material in said solution, cooling the dispersion in the presence of the swellable polymer material until ethylcellulose separates out from the dispersion to form coating walls on and around the core material. The ethylcellulose microcapsules are said to protect the core material effectively and, when administered orally, release the core material rapidly in digestive organs such as the stomach.

GB-A 2 226 804 describes a process for the preparation of microcapsules comprising microencapsulating crystal granules of cyclohexane-insoluble active ingredients in a cyclohexane medium with ethylcellulose in the presence of an anionic surface-active agent or post-treating the drug granules microencapsulated with ethylcellulose by a cyclohexane-dissolved surface-active agent. The microcapsules described in the British patent application can be compressed directly into tablets without any further granulation. The microcapsules are said to provide a rapid release of the active ingredient contained therein.

U.S. Pat. No. 6,531,152 describes a delivery device for immediate localized release of a desired agent in the gastrointestinal tract, said device comprising:
  a core comprising said agent, a core material that swells when exposed to an aqueous liquid, and a disintegrant;
  a rigid coating surrounding said core that disintegrates and bursts when said core swells, said coating comprising water-insoluble hydrophilic particulate matter embedded in a water-insoluble carrier. The examples describe the preparation of coated tablets wherein a tablet core is spray coated with a coating suspension that was prepared by dissolving ethylcellulose in ethanol followed by the addition of calcium pectinate powder.

An important drawback associated with the aforementioned methods for the preparation of microencapsulates resides in the use of organic solvents, notably cyclohexane. In order to allow microcapsules to be used in foodstuffs, beverages and pharmaceuticals, residual levels of organic solvents need to be reduced to very low levels. However, it is very difficult to achieve this and clearly it would be preferable to have no traces of organic solvents in these microcapsules at all.

WO 2008/056344 describes a method of producing microcapsules having a core and a coating encapsulating the core, the method comprising the steps of providing a core-forming fluid stream and a coating-forming fluid stream, providing a two spray nozzle arrangement having an outer nozzle disposed concentrically about a core nozzle, spraying the core-forming fluid stream from the core nozzle and the coat-forming fluid stream from the outer nozzle to produce microcapsules, and solidifying the microcapsules upon formation in a suitable gas. The Examples of the international patent application describes the preparation of microencapsulates by spraying the core-forming fluid stream and the coat-forming fluid stream in an atmosphere of nitrogen, using an inlet temperature of 100° C. Example 5 describes the preparation of a microencapsulate by spray drying a core-forming fluid stream consisting of a solution of sodium diclofenac and sodium fluorescein in ethanol together with a coat-forming fluid stream consisting of a solution of ethylcellulose in ethanol. Drawbacks of the process described in the international patent application are the explosion risks associated with the removal of organic solvents by spray drying and the difficulty of finding and maintaining adequate process conditions for the production of a high quality microencapsulate. Furthermore, due to the fact that the diameter of the core nozzle is typically in the range of 0.7-2 mm and that of the concentric nozzle in the range of 1.4-4 mm, the production of encapsulates having an average diameter in the range of 1-10 µm as disclosed in the examples of WO 2008/056344 is bound to yield encapsulates that will show significant leakage, especially at high payloads. Another problem that has been observed in relation to microcapsules that contain a hydrophobic coating is poor water dispersibility. Poor water dispersibility hampers the utilisation of such microcapsules in aqueous products (e.g. beverages) and may also adversely affect the intestinal release of the active components contained therein.

In addition, there is a need for microencapsulates that are very stable when used in water-containing foodstuffs, beverages, nutritional or pharmaceutical products, but that release their contents after ingestion, e.g. under the influence of the highly acidic conditions within the stomach.

SUMMARY OF THE INVENTION

The inventors have discovered a process that enables the preparation of a microencapsulate that is stable in the presence of water, that does not contain traces of organic solvent and that readily disperses in water. This process employs:
   a fluid composition comprising solvent, dissolved hydrophobic polymer and a dispersed active component; and
   a pressurised antisolvent that is gaseous at atmospheric pressure, said solvent being soluble in or miscible with the antisolvent, said hydrophobic polymer and said active component being insoluble in the antisolvent, and comprises the successive steps of:
a. combining the fluid composition and the antisolvent so as to achieve a condition of super saturation;
b. precipitating the hydrophobic polymer onto the dispersed active component to produce microcapsules in which the active component is fully enveloped by a coating, said microcapsules having a volume weighted average diameter of between 10 nm and 25 µm,
c. collecting the microapsules and separating them from the antisolvent.

The above mentioned process enables the manufacture of microencapsulates that do not contain detectable levels of organic solvent, that can readily be dispersed into water and that do not rapidly release the active component when brought into contact water.

The inventors have surprisingly found that the present invention enables the production of microencapsulates that combine a high payload (e.g. 60 wt. %) with a very high stability in the presence of water. This finding is unexpected as the microcapsules in the present microencapsulate are very small, meaning that at a high payload goes hand in hand with a very thin coating layer. Typically, at payloads of around 50 wt. % the coating layer of the present microencapsulate has a thickness of less than 1-2 µm. It is truly remarkable that microcapsules in which the active ingredient is enveloped by such a thin coating layer can be stored in the presence of water for days without significant leakage of the encapsulated active component.

Another aspect of the invention relates to a novel microencapsulate that may be prepared by means of the above defined process. The microencapsulate of the present invention does not release the encapsulated active component when incorporated in water-containing foodstuffs, beverages, nutritional compositions or pharmaceutical compositions. However, following ingestion, the active component is released rapidly. In addition, the present microencapsulate is readily water-dispersible and capable of surviving the conditions of shear typically employed in the manufacture of foodstuffs and beverages.

The microcapsules contained in the present microencapsulate are characterised in that they comprise:
   a core particle containing an active component; and
   a coating that fully envelops the core particle, containing a hydrophobic polymer; wherein the core particle contains 5-90% by weight of the core particle of a release trigger component and/or the coating contains 3-100% by weight of the hydrophobic polymer of a release trigger component.

The release trigger component employed in the microcapsules is selected from:
   a water-swellable polymer having a water-uptake capacity at 37° C. and pH 7.0 of less than 20 wt. % and a water-uptake capacity at 37° C. and pH 2.0 of at least 50 wt. %; and
   an edible salt having a water solubility at 37° C. and a pH of 7.0 of less than 1 mg/ml and a water solubility at 37° C. and a pH of 2.0 of at least 5 mg/ml.

The stability of the present microencapsulate in most water-containing products is a result of the complete encapsulation of the core particle by a coating that comprises the hydrophobic polymer and optionally a release trigger component that does not let water through at neutral or slightly acidic pH. The instability of the microencapsulate after ingestion results from the presence of the release trigger component in the coating and/or the core particle. When the present microencapsulate is ingested, the release trigger component will cause destabilisation of the microcapsules. The mechanisms involved with this destabilisation include (i) swelling of a polymer; or (ii) osmotic pressure resulting from or dissolution of a salt. Polymer swelling and/or osmotic pressure will cause the coating of the microcapsules to crack, allowing the release of the incapsulated active component. Dissolution of salt contained within the coating will open up channels in the coating through which the active component can be released. The small particle size of the microcapsules favours a rapid release of the active component as soon as a suitable trigger is provided.

Although the inventors do not wish to be bound by theory it is believed that the extremely small particles size of the microcapsules in the present microencapsulate renders the microcapsules readily water-dispersible and also renders them less vulnerable to shear. Water-dispersibility of the present microencapsulate may be further improved by the addition of appropriate surface active agents.

FIGURES

Figure 2:
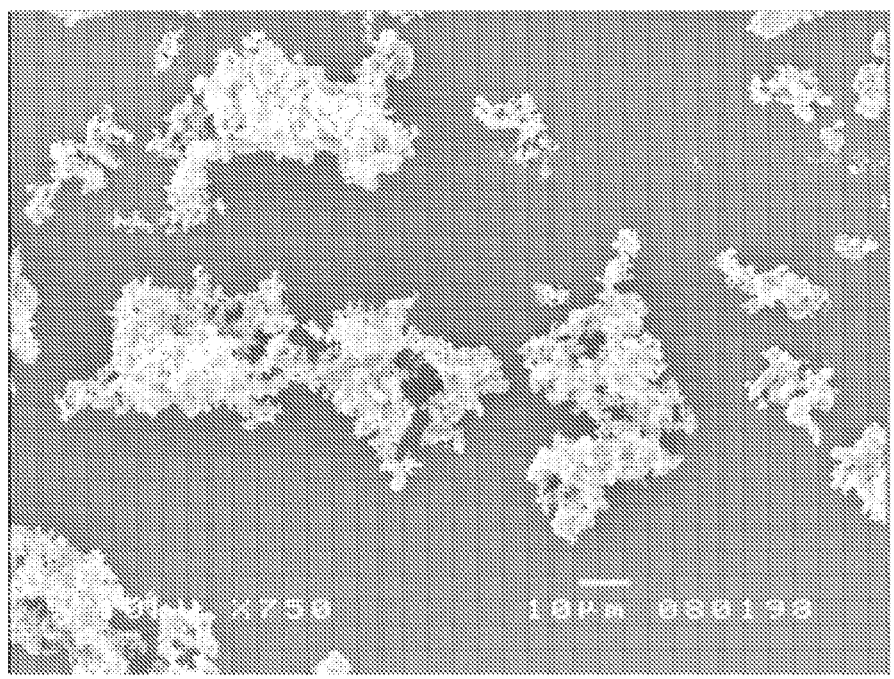

FIG. 1 shows a SEM micrograph of a microencapsulate according to the present invention FIG. 2 shows a SEM micrograph of the same microencapsulate as FIG. 1, but at a lower resolution.

DETAILED DESCRIPTION OF THE INVENTION

Accordingly, one aspect of the invention relates to a microencapsulate comprising at least 40 wt. % of microcapsules having a diameter of 0.1 µm to 25 µm and containing at least 1 wt. % of an active component, said microcapsules comprising:

- a core particle having a diameter of 90 nm to 23 µm, representing 1-75 wt. % of the microcapsule and containing at least 3% of the active component by weight of said core particle; and
- a coating that fully envelops the core particle, representing 25-99 wt. % of the microcapsule and containing at least 20 wt. % of a hydrophobic polymer selected from cellulosic ethers, cellulosic esters, zein, shellac, gluten, polylactides, hydrophobic starch derivatives, polyvinyl acetate polymers, polymers or copolymers derived from an acrylic acid ester and/or a methacrylic acid ester and combinations thereof;

wherein the core particle contains 5-90% by weight of the core particle of a release trigger component and/or the coating contains 3-100% by weight of the hydrophobic polymer of a release trigger component, said release trigger component being selected from:

- a water-swellable polymer having a water-uptake at 37° C. and pH 7.0 of less than 20 wt. % and a water-uptake capacity at 37° C. and pH 2.0 of at least 50 wt. %; and
- an edible salt having a water solubility at 37° C. and a pH of 7.0 of less than 1 mg/ml and a water solubility at 37° C. and a pH of 2.0 of at least 5 mg/ml.

The term "microencapsulate" as used herein refers to a particulate composition in which the microcapsules are contained as non-aggregated particles and/or in the form of aggregated particles composed of clearly distinguishable microcapsules.

The term "microcapsule" as used herein refers to a particle that contains at least a single core particle that is fully enveloped by a coating having a composition and/or structure that is different from that of the core particle.

The term "core particle" as used herein encompasses both solid, semi-solid and liquid particles. The term "core particle" also encompasses composite particles, such as coated particles, and agglomerated particles.

The term "active component" as used herein refers to a substance or a composition having a clearly recognised activity or functionality. Examples of active components include nutritionally relevant components (e.g. minerals, vitamins, carotenoids, polyunsaturated oils), pharmaceutically active components, flavourings, proteins (e.g. enzymes), peptides, amino acids, micro-organisms.

As mentioned herein before, the present invention enables the preparation of microcapsules that are stable in an aqueous environment of neutral pH but that quickly release the active component in an aqueous environment of acidic pH. Consequently, these microcapsules can advantageously be employed in water-containing beverages, foodstuffs or pharmaceutical products as the microcapsules will release the active component under gastric conditions, making the active component available for absorption in the intestines. Thus, a particularly preferred embodiment of the invention relates to a microencapsulate meeting the requirement that at a temperature of 37° C. (i) less than 0.2. % of the active component is released within 1 hour when 20 mg of the microencapsulate is dispersed in 20 ml of distilled water and (ii) at least 5%, preferably at least 30% and most preferably at least 50% of the active component is released within 1 hour when 20 mg of the microencapsulate is dispersed in 20 ml of distilled water of which the pH was previously adjusted to 1.0 with HCl.

The present invention provides microencapsulates that not only are very stable in aqueous environment of neutral or slightly acidic pH but also exhibit a very high encapsulation efficiency. The term "encapsulation efficiency" refers to the fraction of the active component that is effectively entrapped in the microencapsulate. According to a particularly preferred embodiment, the present microencapsulate exhibits an encapsulation efficiency of at least 75%, more preferably of at least 85% and most preferably of at least 95%. The "encapsulation efficiency" as referred to in this document is determined by incorporating an active component, such as iron pyrophosphate, into the core particles of the microcapsules. Next, 20 mg of microencapsulate is dispersed into 20 ml of distilled water. After 1 hour the suspension liquid is centrifuged and a sample is taken from the supernatant. Subsequently, the concentration of the active component (AC) in the sample is determined and the encapsulation efficiency is calculated by means of the following equation: % EE=100%× (encapsulated AC)/(unencapsulated AC+encapsulated AC).

The present invention enables the production of microcapsules having a very high payload. Accordingly, in a very preferred embodiment, the microcapsule contains at least 5 wt. %, more preferably at least 10 wt. % and most preferably at least 20 wt. % of the active component.

According to a preferred embodiment, the microencapsulate of the present invention contains at least 90 wt. %, even more preferably at least 95 wt. % and most preferably at least 99 wt. % of microcapsules having a diameter of 0.1 µm to 25 µm. In accordance with another preferred embodiment, the microencapsulate contains at least 80 wt. %, even more preferably at least 85 wt. % and most preferably at least 90 wt. % of microcapsules having a diameter of 0.2 µm to 20 µm.

The weight averaged mean diameter of the present microencapsulate advantageously lies within the range of 0.2 µm to 10 µm, especially in the range of 0.25 µm to 8 µm and most preferably in the range of 0.3 µm to 6 µm.

The core particle of the microcapsules typically has a diameter of 150 nm to 20 µmm, especially of 200 nm to 15 µm. Advantageously, the core particle represents 5-70 wt. %, most preferably 10-60 wt. % of the microcapsule. The active component is preferably contained in the core particle in an amount of at least 10%, more preferably of at least 30% and most preferably of at least 70% by weight of said core particle. As mentioned herein before, the core particle may be solid, semi-solid or liquid. Preferably, the core particle is solid.

The coating that fully envelops the core particle of the microcapsules typically represents 30-95 wt. %, more preferably 40-90 wt. % of the microcapsule. The hydrophobic polymer advantageously represents at least 20 wt. %, more preferably at least 50 wt. %, even more preferably at least 70 wt. % and most preferably at least 90 wt. % of the coating.

The hydrophobic polymer that is employed in the coating of the microcapsules is advantageously selected from cellulosic ethers, zein, shellac, gluten, polylactides, hydrophobic starch derivatives (such as OSA) and combinations thereof. Even more preferably the hydrophobic polymer is a cellulosic ether, most preferably ethyl cellulose.

The microcapsules of the present invention may comprise one or more core particles. Preferably, said microcapsules contain not more than 5 core particles, even more preferably not more than 3 core particles.

Typically, in the present microcapsules, the hydrophobic polymer and the optional release trigger component together represent at least 90%, preferably at least 95% by weight of the coating.

The microencapsulate of the present invention advantageously contains a release trigger component in the form of an (acid) water-swellable polymer as defined herein. The water-swellable polymer may suitably be incorporated in the core particle, the coating or both.

In accordance with one particular advantageous embodiment the release trigger component contained in the coating of the microcapsules is a water-swellable polymer as defined herein before.

In accordance with another advantageous embodiment, the release trigger component contained in the core particle is a water-swellable polymer as defined herein.

The inventors have found that microcapsules in which the core particles contain the water-swellable polymer are highly stable in aqueous environment at neural pH, but at the same time very efficiently release the active component after ingestion. Thus, a particularly preferred microencapsulate is one in which the core particle contains a water-swellable polymer as defined herein.

Advantageously, the water-swellable polymer of the present invention has a water-uptake at 37° C. and pH 7.0 of less than 10 wt. %, most preferably of less than 5 wt. %. The water-uptake capacity at 37° C. and pH 2.0 of the water-swellable polymer preferably is at least 80 wt. %, most preferably at least 120%.

The water-uptake capacity of the release trigger component is suitably determined by weighing the swollen microcapsules, as described in Biomaterials, 23 p 4469 (2002).

Besides the active component, the hydrophobic polymer and the optional release trigger component the microcapsules in the microencapsulate can suitably contain other components. Preferably, however, the active component, the hydrophobic polymer and the release trigger component represent the bulk of the microcapsule. Accordingly, in a preferred embodiment the active component, the release trigger component and the hydrophobic polymer together represent at least 80 wt. %, preferably at least 90 wt. % of the microencapsules.

The release trigger component in the form of an edible salt is advantageously a salt having a water solubility at 37° C. and a pH of 7.0 of less than 0.4 mg/ml, preferably of less than 0.1 mg/ml and a water solubility at 37° C. and a pH of 2.0 of at least 10 mg/ml, preferably of at least 20 mg/ml. Preferably, the edible salt is selected from carbonates, phosphates, sulphites, citrates, oxalates, succinate, fumarate and combinations thereof. The latter salts are hardly soluble in water of neutral pH, but are much more soluble under acidic conditions. Thus, when the microcapsules come in contact with water of acidic pH they will absorb water and will at least partially dissolve thereby creating pores in the coating that will allow the active component to be released from the microcapsules.

The release trigger component in the form of a water-swellable polymer is preferably an amino-group containing polymer, even more preferably an amino-group containing polymer selected from chitosan, aminoalkyl methacrylate copolymers, polyvinyl aminoacetate and combinations thereof. The latter cationic water-swellable polymers will easily disperse/dissolve in water of acidic pH as they carry a positive charge at such pH.

The benefits of the present microencapsulate can be realised with a wide range of active components. Preferably, the active component is water-soluble and/or water-dispersible. Even more preferably, the active component is water-soluble. The active component is preferably selected from minerals, vitamins, pharmaceutically active substances, micro-organisms (e.g. probiotics), sterols, carbohydrates, proteins (e.g. enzymes), peptides, amino acids, carotenoids, anti-oxidants, extracts, bitter tasting substances, oils and combinations thereof. More preferably, the active component is selected from minerals, vitamins, probiotics, enzymes and combinations thereof. Even more preferably, the active component is a mineral, most preferably a mineral selected from the group consisting of iron compounds, calcium compounds, magnesium compounds, zinc compounds, iodine and combinations thereof.

The benefits of the present invention are particularly pronounced in microencapsulates essentially consisting of microcapsules having a weight averaged diameter of less than 10 μm and wherein said microcapsules are present as individual non-aggregated particles and/or in the form of aggregates. Accordingly, in an especially preferred embodiment, the microencapsulate consists of a powder having a weight averaged diameter of less than 10 μm or it consists of an agglomerated powder having a weight averaged diameter in the range of 10-1000 μm.

Another aspect of the invention relates to a process of encapsulating an active component in a matrix comprising a hydrophobic polymer by employing:

a fluid composition comprising at least 80 wt. % of solvent, 0.1-20 wt. % of dissolved hydrophobic polymer and 0.002-20 wt. %, preferably 0.2-20 wt. % of a dispersed active component; and an antisolvent that is gaseous at atmospheric pressure, said antisolvent having a pressure of at least 70 bar, said solvent being soluble in or miscible with the antisolvent, said hydrophobic polymer and said active component being insoluble in the antisolvent, and said hydrophobic polymer having a water solubility at 20° C. of less than 0.1 mg/ml, preferably of less than 0.05 mg/ml;

wherein the process comprises the successive steps of:

a. combining the fluid composition and the antisolvent so as to achieve a condition of super saturation;

b. precipitating the hydrophobic polymer onto the dispersed active component to produce microcapsules in which the active component is fully enveloped by a coating, said microcapsules having a volume weighted average diameter of between 100 nm and 25 μm;

c. collecting the microcapsules and separating them from the antisolvent.

The above defined process is particularly useful for manufacturing a microencapsulate as defined herein before. Unlike microencapsulation processes described in the prior art, the present process enables the manufacture of a microenpasulate having a very high encapsulation efficiency without the need of using washing steps to remove badly encapsulated material.

Thus, in accordance with a particularly preferred embodiment, the microencapsulate that is directly obtained after separation from the antisolvent has an encapsulation efficiency of at least 90%, most preferably of at least 95%.

The use of an antisolvent in the form of a pressurised gas offers the advantage that no significant levels of this antisolvent will be retained in the isolated microcapsules. Furthermore, this antisolvent facilitates very efficient extraction of the solvent that is used to dissolve hydrophobic polymer. Solvents that are particularly suited for use in the present method include $C_1$-$C_4$ alkanols, $C_1$-$C_4$ diols, $C_1$-$C_4$ triols, water and combinations thereof. According to a particularly preferred embodiment, the solvent is selected from methanol, ethanol, n-propanol, iso-propanol, water and combinations thereof. Most preferably, the solvent consists of ethanol or a mixture of ethanol and water.

According to a particularly preferred embodiment of the present process, the fluid composition additionally contains a dissolved or dispersed release trigger component as defined herein before in an amount of 1-100%, preferably 3-100% by weight of the hydrophobic polymer.

The dispersed active component may be liquid, semi-solid or solid. Preferably, the dispersed active component is solid at ambient temperature (20° C.).

The antisolvent employed in the present process may consist of a single substance or alternatively it may consist of a mixture of substances. Thus, the antisolvent may comprise a mixture of pressurised gases, optionally in combination with one or more liquid components. The antisolvent may suitably contain co-solvents up to a level of 10 wt. %, preferably up to a level of not more than 5 wt. %. Examples of suitable co-solvents include ethanol, methanol, acetone, iso-pronanol and combinations thereof.

According to a particularly preferred embodiment, the antisolvent is a supercritical or nearcritical fluid having a pressure of at least $0.3 \times P_c$ and a temperature of at least $T_c - 60°$ C., $P_c$ representing the critical pressure of the main gaseous component in the antisolvent and $T_c$ representing the critical temperature of that main gaseous component.

The supercritical, subcritical or nearcritical fluid employed in the present process is preferably selected from carbon dioxide, nitrous oxide, ethane, ethylene propane, cyclopropane, propylene, butane, argon, nitrogen and mixtures thereof. According to a particularly preferred embodiment, the antisolvent contains at least 60 wt. % of carbon dioxide.

The fluid composition employed in the present process may contain additional dissolved components besides the hydrophobic polymer and the optional release trigger component, e.g. stabilisers, colouring, antibiotics, antifungal agents or antioxidants. Typically, the solvent, the dissolved hydrophobic polymer and the dispersed active component together represent at least 90 wt. % of the fluid composition. Preferably, together they represent at least 95 wt. % of the fluid composition.

In the present process the fluid composition is advantageously combined with the antisolvent by spraying the fluid composition into a mixing chamber containing the antisolvent, e.g. by releasing it through a nozzle with a relatively large diameter (e.g. of more than 1 mm). The use of a nozzle with a relatively large diameter offers the advantage that the fluid composition is not broken upon introduction into the mixing chamber.

In the present process the fluid composition and the antisolvent are typically admixed in a weight ratio within the range of 1:1000 to 1:10, preferably in a weight ratio within the range of 1:200 to 1:50.

In the present process contact time between antisolvent and the microcapsules is preferably kept as short as possible in order to prevent that components (e.g. the active component) are extracted from these microcapsulates. Typically, average contact time between microcapsules and antisolvent does not exceed 3 hours. More preferably, said contact time does not exceed 60 minutes. Even more preferably the contact time does not exceed 30 minutes, most preferably it does not exceed 10 minutes.

According to a particularly preferred embodiment, the microcapsules are separated from the antisolvent whilst formation of new microcapsules continues. This may be achieved, for instance, with the help of a cyclone or by collecting the particles in a medium that is immiscible with antisolvent.

In a preferred embodiment of the present process, following separation of the antisolvent, the extracted solvent is removed from the antisolvent and the antisolvent is recirculated to step a. of the process. Thus, the total amount of antisolvent employed in the process may be minimised without significant adverse effects on process efficiency or encapsulate quality. In a particularly preferred embodiment, the extracted solvent is effectively removed in a highly selective fashion. By removing the solvent and not, for instance, dissolved components of the fluid composition, undesired extraction of these components from the microcapsules may be avoided.

The solvent may be removed effectively from the antisolvent by employing an adsorbent or absorbent that adsorbs/absorbs the solvent but not the antisolvent.

Alternatively, the solvent is removed by reducing the pressure or temperature of the solvent-containing antisolvent to allow the solvent to condense. It is also feasible to remove the solvent by using selective membranes. Following separation of the antisolvent from the condensed solvent, the antisolvent is repressurised before being recirculated to step a.

The fluid composition of the present process is suitably formed by combining the solvent with the active component, the hydrophobic polymer and optionally other components, accompanied by or followed by homogenisation.

The invention is further illustrated by means of the following, non-limiting examples.

EXAMPLES

Example 1

Ethylcellulose (2.7 g, Ethocel® 100, The Dow Chemical Company) was dissolved into ethanol (87.3 g) by dispersing it in the solvent and applying stirring using an IKA® Ultra-Turrax for 1 min followed by sonication for 20 min.

Subsequently powdered iron pyrophosphate (1.22 g) having a mean particle size smaller than 5 µm, was dispersed into the solution after which the dispersion was stirred using the above mentioned high shear mixing device for 5 min.

The dispersion was rapidly transferred into a syringe pump, Isco® 260D, from which the dispersion was pumped into a high pressure vessel via the inside tube of a coaxial nozzle (Spraying systems Co., model 2050/64), that was mounted at the top of the vessel. The high pressure vessel was 4 litres in volume. Before pumping in the solution the vessel was pressurized with $CO_2$ to 115 bar using a membrane pump (Orlita®). The $CO_2$ entering the high pressure vessel was heated to 55° C. The vessel was heated to 55° C., through an oil-heated jacket. The vessel was equipped with a stainless steel sintered filter, which was mounted at the bottom of the vessel.

In total 36.8 ml of dispersion was added to the vessel at a rate of 2.5 ml/min. $CO_2$ was simultaneously added to the top of the vessel through the outer passage of the coaxial nozzle at a rate of 500 g/min. The $CO_2$ was removed via a tube the bottom of the vessel. The pressure in the vessel was controlled via a valve connected to that tube. After spraying the dispersion, the vessel was flushed with $CO_2$ for another 20 min before pressure was released. A powder predominantly consisting of microcapsules smaller than 5 µm, largely aggregated to fibrous material was collected from the filter.

The release of iron from the powder so obtained was investigated in water and in a 0.1N HCl solution by dispersing 50 mg of the powder in 20 g water or acid solution, respectively. Samples from the acid solution were taken after 1 h and 4 h. A sample from water was taken after 8 days. Results are shown in Table 1.

TABLE 1

| Medium | Fe released (ppm) | Fe released (%) |
|---|---|---|
| 0.1N HCl - 1 hour | 13.01 | 5.2% |
| 0.1N HCl - 4 hours | 29.8 | 11.9% |
| Water (neutral) - 8 days | 0.38 | 0.2% |

Example 2

The iron containing microencapsulate described in Example 1 was applied in margarine. The microencapsulate powder was dispersed in the aqueous phase of the margarine to provide 3 mg of iron per 20 g of margarine. In the same fashion a margarine containing the same amount of supplemented iron was prepared using the non-encapsulated iron pyrophosphate powder described in Example 1.

The microencapsulate powder could easily be dispersed and was not visible in the mixture. The margarine containing the microencapsulate remained stable for at least 8 weeks upon storage at 4° C., as determined through the smell and colour of the margarine. In contrast, the margarine containing non-encapsulated iron pyrophosphate developed a perceptible off-flavour after only one day.

Example 3

A microencapsulate containing solid iron(III) pyrophosphate was made as follows:

Ethyl cellulose (Ethocel® 100 premium) was dissolved into ethanol by dispersing it in the solvent and applying stirring using a IKA® Ultra-Turrax for 1 minute followed by sonication for 20 min. Separately, an aqueous solution was made comprising of 1.85% chitosan and 4.65% acetic acid. Subsequently fine powdered iron pyrophosphate (5%) was dispersed into this acidic aqueous solution. The dispersion was stirred using the above mentioned high shear mixing device for at least 5 minutes.

Subsequently, the ethyl cellulose solution was mixed with the aqueous chitosan dispersion using the above mentioned high shear mixing device for 5 minutes. Upon mixing, an emulsion was formed in which the iron pyrophosphate remained dispersed as a solid phase. The formed emulsion contained: 1.31% Fe, 0.49% chitosan and 1.1% ethyl cellulose.

The emulsion was rapidly transferred into a syringe pump, Isco® 260D, from which the dispersion was pumped into a high pressure vessel via the inside tube of a coaxial nozzle (Spraying Systems®, 1650/64), that was mounted at the top of the vessel. The high pressure vessel was 4 litres in volume. Before pumping in the solution, the vessel was pressurized with $CO_2$ to 125 bar using a membrane pump (Orlita). The $CO_2$ entering the high pressure vessel was heated to 48° C. The vessel was heated to 48° C. as well, through an oil-heated jacket. The vessel was equipped with a stainless steel sintered filter, which was mounted at the bottom of the vessel.

In total 59.66 ml of emulsion was added to the vessel at a rate of 1 ml/min. $CO_2$ was simultaneously added to the top of the vessel through the outer passage of the coaxial nozzle at a rate of 500 g/min. The $CO_2$ was removed via a tube the bottom of the vessel. The pressure in the vessel was controlled via a valve connected to that tube After spraying the dispersion, the vessel was flushed with $CO_2$ for another 15 min before pressure was released. A powder was collected from the filter.

Example 4

The release of iron from microencapsulate obtained by the procedure described in Example 3 was investigated in distilled water and in a 0.1 M HCl solution by dispersing 20 mg microencapsulate in 20 g water or acid solution, respectively. Samples from the acid solution were taken after 1 h and 4 h and analysed via ICP-MS. Samples from the distilled water were collected and analysed after 1 and 4 hours. Results are shown in the table below.

| Medium | Fe released (ppm) | % Fe released |
|---|---|---|
| 0.1N HCl - 1 hour | 40.4 | 50.6 |
| 0.1N HCl - 4 hours | 47.6 | 59.5 |
| Water - 4 hours | 0.0 | 0.0 |

Example 5

Chitosan—low molecular weight (1.85%) was dissolved into an aqueous solution of acetic acid (4.8%) by dispersing and further stirring it using an IKA® Ultra-Turrax for 10 min followed by sonication for 30 min. Subsequently fine powdered iron lactate was dispersed into the above mentioned readymade solution after which the dispersion was stirred using the same high shear mixing device for at least 10 min.

The dispersion was rapidly transferred into a syringe pump, Isco® 260D, from which the dispersion was pumped into a high pressure vessel via the inside tube of a coaxial nozzle, that was mounted at the top of the vessel. The high pressure vessel was 4 litres in volume. Before pumping in the solution the vessel was pressurized with carbon dioxide to 150 bar using a membrane pump (Orlita®). The carbon dioxide entering the high pressure vessel was heated to 50° C. The vessel was heated to 50° C., through an oil-heated jacket. The vessel was equipped with a stainless steel sintered filter, which was mounted at the bottom of the vessel.

In total 86.70 ml of dispersion was added to the vessel at a rate of 1 ml/min. Carbon dioxide was simultaneously added to the top of the vessel through the outer passage of the coaxial nozzle at a rate of 722 g/min. The carbon dioxide was removed via a tube the bottom of the vessel. The pressure in the vessel was controlled via a valve connected to that tube After spraying the dispersion, the vessel was flushed with $CO_2$ for another 20 min before pressure was released. An iron lactate-chitosan powder was collected from the filter.

Subsequently, the iron lactate-chitosan powder was further dispersed in a solution comprise of Ethocel® (Dow-Standard 100 premium) in ethanol. The ethylcellulose (Ethocel Standard 100 premium) was dissolved into ethanol in a concentration of 1.5 wt. % by dispersing it in the solvent and applying stirring using an IKA® Ultra-Turrax for 1 min followed by sonication for 20 min.

The dispersion was rapidly transferred into a syringe pump, Isco® 260D, from which the dispersion was pumped simultaneously with carbon dioxide into a high pressure vessel via a heated pipe mounted at the top of a 4 L (in volume) pressurised vessel. The pipe is provided with a T mixer with two 0.3 mm nozzles (one for the carbon dioxide line and one for the solution line) as described in EP-A 1 494 796. Before pumping in the mixture of carbon dioxide and solution the vessel was pressurized with carbon dioxide to 120 bar using a membrane pump (Orlita®). The carbon dioxide entering the high pressure vessel was heated to 40° C. The vessel was heated to 40° C., through an oil-heated jacket. The vessel was equipped with a stainless steel sintered filter, which was mounted at the bottom of the vessel.

In total 37.44 ml of dispersion was added to the vessel at a rate of 6 ml/min. Carbon dioxide was simultaneously added via the T mixer with a similar Isco® 260D pump (with a flow rate of 6 mL/min). but also from the top of the big vessel through the outer passage with a flow rate of 416 g/min. The carbon dioxide was removed via a tube the bottom of the vessel. The pressure in the vessel was controlled via a valve connected to that tube After spraying the dispersion, the vessel was flushed with carbon dioxide for another 20 min before pressure was released. An iron lactate-chitosan-ethylcellulose powder was collected from the filter.

Example 6

The release of iron from the microencapsulate obtained by the procedure described in Example 5 was investigated in distilled water and in a 0.1M HCl solution by dispersing 0.02 g in 20 g of distilled water or acid solution, respectively. Samples from the distilled water and the acid solution were taken after 1 h and 4 h. Results are shown in the table below.

| Medium | Fe released (ppm) | % Fe released |
|---|---|---|
| 0.1M HCl - 1 hour | 8.57 | 102.6% |
| 0.1M HCl - 4 hours | 8.37 | 100.9% |
| Distilled water - 1 hour | 0.02 | 0.24% |
| Distilled water - 4 hours | 0.59 | 7.06% |

Example 7

Ethylcellulose 1.5 wt. % Ethocel® Standard Premium 100, ex Dow) was dissolved into ethanol by dispersing it in the solvent and applying stirring using a IKA® Ultra-Turrax for 1 minute followed by sonication for 20 minutes. Subsequently, fine powdered iron pyrophosphate (3%) was dispersed into the solution after which the dispersion was stirred using the above mentioned high shear mixing device for 5 minutes.

The dispersion was rapidly transferred into a syringe pump, Isco® 260D, from which the dispersion was pumped into a high pressure vessel via a long pipe provided on top with a two nozzle (each of 0.1 mm) T mixer as described in EP-A 1 494 796. From one nozzle of the T mixer the Fe-pyrophosphate suspension in Ethocel solution was pumped and from the opposite nozzle $CO_2$ was pumped into the long pipe. The high pressure vessel was 4 litres in volume. Before pumping in the solution the vessel was pressurized with $CO_2$ to 120 bar using a membrane pump (Orlita®). The $CO_2$ entering the high pressure vessel was heated to 40° C. The vessel was heated to 40° C., through an oil-heated jacket. The vessel was equipped with a stainless steel sintered filter, which was mounted at the bottom of the vessel.

In total 120 ml of dispersion was added to the vessel at a rate of 6 ml/min. $CO_2$ was simultaneously added to the top of the pipe (with a rate of 15 mL/min) and through the outer passage of the 4 Lvessel with a rate of 25 kg/h. The $CO_2$ was removed via a tube the bottom of the vessel. The pressure in the vessel was controlled via a valve connected to that tube. After spraying the dispersion, the vessel was flushed with $CO_2$ for another 10 min before pressure was released. A powder was collected from the filter.

SEM micrographs of this powder are depicted in FIGS. 1 and 2. These micrographs show that the microencapsulate comprised agglomerates of spherical micronic-nano particles.

Example 8

A water insoluble microencapsulate containing a phospholipid rich oil from a maritime source as the active component was made as follows:

Chitosan (1%) was dissolved into an aqueous solution of acetic acid (0.5%) by dispersing and further stirring it using a IKA® Ultra-Turrax for 10 min. The solution was then warmed with a hot water bath to approximately 40-50° C. and maltodextrin MD20(7%) was subsequently added and dissolved by stirring with a stirrer for 10 min and further stirring using the same high shearing device for 5 min. The marine oil (2%) was then added to the aqueous solution and the solution was mixed with the same high shearing device for 5 min to form an oil-in-water emulsion.

Immediately after mixing, the emulsion was transferred into a high pressure syringe pump, from which the dispersion was pumped into a high pressure vessel via the inside tube of a coaxial nozzle, that was mounted at the top of the vessel. The high pressure vessel was 4 litres in volume. Before pumping in the solution the vessel was pressurized with carbon dioxide to 150 bar using a membrane pump. The carbon dioxide entering the high pressure vessel was heated to 40° C. The vessel was heated to 40° C., through an oil-heated jacket. The vessel was equipped with a stainless steel sintered filter, which was mounted at the bottom of the vessel.

In total 38.65 ml of dispersion was added to the vessel at a rate of 0.75 ml/min. Carbon dioxide was simultaneously added to the top of the vessel through the outer passage of the coaxial nozzle at a rate of 500 g/min. The carbon dioxide was removed via a tube the bottom of the vessel. The pressure in the vessel was controlled via a valve connected to that tube. After spraying the dispersion, the vessel was flushed with $CO_2$ for another 20 min before pressure was released. An oil/chitosan/MD20 powder was collected from the filter. This powder contained virtually no free fat, i.e. most of the fat was effectively encapsulated in the chitosan/MD20 matrix.

Subsequently, the oil/chitosan/MD20 powder was dispersed in an ethanolic solution of ethylcellulose (Ethocel®, Dow-Standard 100 premium) using a IKA® Ultra-Turrax for 1 min, followed by sonication for 20 min. The dispersion so obtained contained 2.5 wt. % of the oil/chitosan/MD20 powder and 1.5 wt. % of ethylcellulose.

The latter dispersion was rapidly transferred into a syringe pump from which the dispersion was pumped simultaneously with carbon dioxide into a high pressure vessel via a heated pipe mounted at the top of a 4 L (in volume) pressurised vessel. The pipe was provided with a T mixer with a 0.3 mm nozzle (for the dispersion) and a ¼ in. stainless steel tubing (for the $CO_2$) as described in EP-A 1 494 796. Before pumping in the mixture of carbon dioxide and dispersion the vessel was pressurized with carbon dioxide to 120 bar using a membrane pump. The carbon dioxide entering the high pressure vessel was heated to 40° C. The vessel was heated to 40° C., through an oil-heated jacket. The vessel was equipped with a stainless steel sintered filter, which was mounted at the bottom of the vessel.

In total 43.60 ml of dispersion was added to the vessel at a rate of 6 ml/min. Carbon dioxide was simultaneously added via the T mixer with a similar high pressure syringe pump (at a flow rate of 6 ml/min), and also from the top of the big vessel through the outer passage with a flow rate of 416 g/min. The carbon dioxide was removed via a tube the bottom of the vessel. The pressure in the vessel was controlled via a valve connected to that tube. After spraying the dispersion, the vessel was flushed with carbon dioxide for another 20 min before pressure was released. A free flowing oil/chitosan/MD20/ethylcellulose powder was collected from the filter. Microscopic analysis revealed that over 90 vol. % of the particles was smaller than 15 μm.

The powder neither had an oily smell in a dry state nor did it produce such a smell or taste after being dispersed in water. Microscopy and Raman analysis revealed that oil was released when the powder is dispered in an acid aqueous solution having a pH of 1.5.

Example 9

Example 5 was repeated, except that this time, instead of a dispersion of iron lactate, an aqueous dispersion of 0.1% tricalcium phosphate (release trigger component) and 1% of a bitter peptide from a dairy source was prepared. In addition, no chitosan was added and the concentration of acetic acid was changed to 3%.

The powder obtained by spraying the aforementioned dispersion into the vessel containing highly pressurized carbon dioxide, was subsequently coated by dispersing the powder into an ethanolic solution of ethylcellulose, thereby producing a dispersion containing both components in a concentration of 1.5 wt. %, and by further processing this dispersion as described in Example 5.

A fine free-flowing off-white powder was produced that did not taste bitter, acidic or salty. Also a dispersion of the powder in water of neutral pH was found to be tasteless. This powder is stable in aqueous environment of neutral pH, but releases the encapsulated peptide when brought into a highly acidic aqueous medium.

The invention claimed is:

1. A process of encapsulating an active component in a microcapsule, the process comprising:

(a) combining (i) a fluid composition comprising at least 80 wt. % of solvent, 0.1-20 wt. % of dissolved hydrophobic polymer, 0.002-20 wt. % of a dispersed active component and 1-100% by weight of the hydrophobic polymer, a dissolved or dispersed release trigger component selected from: (A) an amino-group containing water-swellable polymer having a water-uptake capacity at 37°C. and pH 7.0 of less than 20 wt. % and a water-uptake capacity at 37°C. and pH 2.0 at least 50 wt. %; and (B) an edible salt having a water solubility at 37°C and a pH of 7.0 less than 1 mg/ml and a water solubility at 37°C. and a pH of 2.0 of at least 5 mg ml; and (ii) an antisolvent that is gaseous at atmospheric pressure and has a pressure of at least 70 bar so as to achieve a condition of super saturation;

(b) precipitating the hydrophobic polymer and release trigger component onto the dispersed active component to produce microcapsules in which the active component is enveloped by a coating comprising at least 20 wt. % of the hydrophobic polymer, the microcapsules having a volume weighted average diameter of between 10 nm and 25 μm, (c) collecting the microcapsules, wherein the solvent is soluble in or miscible with the antisolvent, wherein the hydrophobic polymer and said active component are insoluble in the antisolvent, wherein the hydrophobic polymer has a water solubility at 20° C. of less than 0.1 mg/ml, and wherein the active component is selected from the group consisting of minerals, vitamins, carotenoids, polyunsaturated oils, pharmaceutically active components, flavourings, proteins, peptides, amino acids, micro-organisms and combinations thereof; and the hydrophobic polymer is selected from the group consisting of cellulosic ethers, cellulosic ethers, zein, shellac, gluten, polylactide, hydrophobic starch derivatives, polyvinyl acetate polymers, polymers or copolymers derived from an acrylic acid ester and/or a methacrylic acid ester and combinations thereof.

2. The process according to claim 1, wherein the solvent is selected from the group consisting of $C_1$-$C_4$ alkanols, $C_1$-$C_4$ diols, $C_1$-$C_4$ triols, water and combinations thereof.

3. The process according to claim 2, wherein the solvent is selected from the group consisting of methanol, ethanol, n-propanol, iso-propanol, water and combinations thereof.

4. The process according to claim 1, wherein the antisolvent is a supercritical or near critical fluid.

5. The process according to claim 1, wherein the fluid composition comprises an amino-group containing a water-swellable polymer having a water-uptake capacity at 37°C. and pH 7.0 of less than 20 wt. % and a water-uptake capacity at 37°C. and pH 2.0 of at least 50 wt. %.

* * * * *